United States Patent
Guo et al.

(10) Patent No.: US 10,746,638 B2
(45) Date of Patent: Aug. 18, 2020

(54) DIRECT METHOD FOR MANUFACTURING LARGE MODEL FRACTURED CORE AND MAINTAINING ORIGINAL OIL-WATER SATURATION

(71) Applicant: SOUTHWEST PETROLEUM UNIVERSITY, Chengdu (CN)

(72) Inventors: Ping Guo, Chengdu (CN); Shuai Wu, Chengdu (CN); Wanbo Zhang, Chengdu (CN); Yisheng Hu, Chengdu (CN); Yijian Chen, Chengdu (CN); Huimin Zhang, Chengdu (CN); Zhouhua Wang, Chengdu (CN); Jianfen Du, Chengdu (CN); Huang Liu, Chengdu (CN); Hongmei Ren, Chengdu (CN)

(73) Assignee: SOUTHWEST PETROLEUM UNIVERSITY, Chengdu (CN)

( * ) Notice: Subject to any disclaimer, the term of this patent is extended or adjusted under 35 U.S.C. 154(b) by 357 days.

(21) Appl. No.: 15/775,391

(22) PCT Filed: Dec. 2, 2016

(86) PCT No.: PCT/CN2016/108425
§ 371 (c)(1),
(2) Date: May 11, 2018

(87) PCT Pub. No.: WO2017/161916
PCT Pub. Date: Sep. 28, 2017

(65) Prior Publication Data
US 2018/0348105 A1    Dec. 6, 2018

(30) Foreign Application Priority Data
Mar. 22, 2016 (CN) .......................... 2016 1 0164743

(51) Int. Cl.
| G01N 15/08 | (2006.01) |
| G01N 1/36 | (2006.01) |
| G01N 33/24 | (2006.01) |
| G01N 1/28 | (2006.01) |

(52) U.S. Cl.
CPC .............. *G01N 1/36* (2013.01); *G01N 15/082* (2013.01); *G01N 15/088* (2013.01); *G01N 33/241* (2013.01); *G01N 2001/2873* (2013.01); *G01N 2001/366* (2013.01)

(58) Field of Classification Search
CPC ....................................................... G01N 1/36
USPC ........................................................ 73/152.07
See application file for complete search history.

(56) References Cited

U.S. PATENT DOCUMENTS

| 4,524,604 A * | 6/1985 | Vondran ............. G01N 15/0806 249/183 |
| 4,751,646 A * | 6/1988 | Alger ...................... E21B 49/02 324/376 |
| 2015/0369718 A1* | 12/2015 | Chertov ............. G01N 15/0806 73/38 |

FOREIGN PATENT DOCUMENTS

| CN | 102053026 A | 5/2011 |
| CN | 102608011 A | 7/2012 |
| CN | 102866043 A | 1/2013 |
| CN | 103983489 A | 8/2014 |
| CN | 105300770 A | 2/2016 |
| CN | 105842026 A | 8/2016 |

OTHER PUBLICATIONS

Ping Guo, et al; Evaluation research on enhanced-gas injection on low-permeability fractured sandstone reservoir; Journal of Oil and Gas Technology( Journal of Jianghan Petroleum Institute ); Oct. 31, 2011; vol. 33, No. 10; p. 139-141.

* cited by examiner

*Primary Examiner* — Walter L Lindsay, Jr.
*Assistant Examiner* — Philipmarcus T Fadul
(74) *Attorney, Agent, or Firm* — Bayramoglu Law Offices LLC

(57) ABSTRACT

A direct method for manufacturing a large model fractured core and maintaining original oil-water saturation, including the following steps: (1) determining the volume V, porosity φ, permeability K, oil saturation $S_o$, water saturation $S_w$ and the like of a fractured core to be manufactured; (2) preparing simulated oil, and determining the used oil mass $m_o = V_o \times \rho_o$; (3) under the circumstance of no consideration of oil saturation, acquiring the mass of the used water, cement and quartz sand; (4) while establishing oil saturation, acquiring the mass $m_w$ of water for manufacturing the core as $m_w = a - V_o \times \rho_w$; (5) mixing oil, water and an emulsifier evenly to prepare an oil-in-water emulsion; (6) adding cement and quartz sand into the emulsion and stirring evenly to obtain cement slurry; (7) when a cement sample is in a semi-solidified state, cutting the cement sample with a steel wire; and (8) solidifying the cement sample to the end.

4 Claims, No Drawings

DIRECT METHOD FOR MANUFACTURING LARGE MODEL FRACTURED CORE AND MAINTAINING ORIGINAL OIL-WATER SATURATION

CROSS REFERENCE TO RELATED APPLICATIONS

This application is the national phase entry of International Application PCT/CN2016/108425, filed on Dec. 2, 2016, which is based upon and claims priority to Chinese Patent Application No. 201610164743.1, filed on Mar. 22, 2016, the entire contents of which are incorporated herein by reference.

TECHNICAL FIELD

The present invention relates to a direct method for manufacturing a large model fractured core and maintaining original oil-water saturation in indoor simulation experiments of petroleum exploration and development.

BACKGROUND

Physical simulation is an important means of simulating the development of oil and gas reservoirs. It is indicated through practices that the larger the mold geometry, the closer the experimental results are to the actual mine field. Experimental cores are divided into natural and artificial ones. Natural cores are hardly obtained and relatively high in cost. So, artificial cores are commonly used to perform large-scale physical simulation. A sand-packed mold fails to simulate a fracture-pore type reservoir owing to low working pressure. Epoxy resin and aluminum phosphate are generally selected as existing cemented mold binders, but most of them require high-temperature sintering. In order to simulate a reservoir development process better, it is necessary for the artificial core to keep original oil-water saturation of the reservoir. With respect to a fractured core, the steps of creating fractures first and establishing saturation subsequently are generally used. Because fluids flow turbulently according to the fractures when saturated, the original water saturation cannot be established. There are two main methods for creating fractures in a large artificial core. In the first method, a metal sheet is inserted prior to the formation of the core and then pulled out to form fractures, but the occasion to pull the metal sheet out is hardly grasped. In the second method, a specific material is placed in a mold in advance, and then melted, dissolved and volatized by means of physical means, but residues will appear and the process is cumbersome.

In order to simulate the reservoir development process better, a physical mold needs to be similar to an actual reservoir, that is, the original oil-water saturation of the reservoir needs to be maintained. Methods for establishing the saturation include a drying method, a centrifugation method, and a displacement method. Both the drying method and the centrifugation method lead to the problem of uneven distribution of water in the core. The displacement method mainly refers to evacuating the core, filling water till saturated, and displacing the water with a reservoir fluid to establish the oil-water saturation. Due to the presence of fractures in the fractured core, the water saturation is often higher than a desired value, such that the desired oil-water saturation cannot be established.

SUMMARY

Technical Problem

An objective of the present invention is to provide a direct method for a large model fractured core and maintaining original oil-water saturation. The method is simple in used materials, low in cost and simple in operation, and can be used to control the distribution of fractures in a core and achieve simultaneous establishment of a mold and saturation. The manufactured core can satisfy high temperature and high pressure experiments and can simulate the reservoir development process better.

Technical Solution

To fulfill the above technical objective, the present invention provides the following technical solution.

A direct method for manufacturing a large model fractured core and maintaining original oil-water saturation sequentially comprises the following steps:

(1) determining the volume V, porosity $\varphi$, permeability K, oil saturation $S_o$ and water saturation $S_w$ of a fractured core to the manufactured, and determining an oil volume $V_o$ of the core as $V_o = V \times \varphi \times S_o$, and a water volume $V_w$ of the core as $V_w = V \times \varphi \times S_w$, wherein the sum of the oil volume and the water volume is a pore volume of the core;

(2) preparing simulated oil according to an oil-water viscosity ratio of the formation under experimental conditions, and determining the oil density as $\rho_o$ and the water density as $\rho_w$, thereby determining the mass $m_o$ of oil for manufacturing the core as $m_o = V_o \times \rho_o$;

(3) under the circumstance of no consideration of oil saturation; acquiring, through experiments, a water-cement ratio m and a cement-quartz sand ratio n based on the porosity $\varphi$ and the permeability K, wherein the water-cement ratio is a mass ratio of water to cement, ranging from 0.3 to 0.5, and the cement-quartz sand ratio is a mass ratio of cement to quartz sand, ranging from 1:1 to 1:3; and thus acquiring the mass of the used water, cement and quartz sand, i.e. a, b and c respectively, under the circumstance of no consideration of oil saturation, i.e., the water saturation is 100%;

(4) under the circumstance of no consideration of oil saturation, filling pores of the core with water, such that $V_o$ and $V_w$ are both filled with water, and the water consumption at this time is a; while establishing oil saturation, continuing to fill $V_w$ with water, and replacing fluid, i.e., water in $V_o$ with oil, wherein the water volume is reduced by $V_o$ compared to that before the oil saturation is established, and the consumption of water for manufacturing the core should be reduced by $V_o \times \rho_w$; and thus acquiring the mass $m_w$ of water for manufacturing the core as $m_w = a - V_o \times \rho_w$;

(5) mixing oil, water and an emulsifier evenly to prepare an oil-in-water emulsion, wherein the emulsifier accounts for 0.16% to 0.21% of the mass sum of oil and water and is a mixture prepared from sorbitan monooleate (Span-80) and polyoxyethylene sorbitan monooleate (Tween-80) according to a mass ratio of 1:10;

(6) adding cement and quartz sand into the emulsifier in the step (5) and stirring evenly to obtain cement slurry, wherein the cement is Portland cement, and the quartz sand has a particle size of 80-120 mesh;

(7) applying simulated oil to the inner surface of a core mold, such that a thin oil film is formed on the inner surface of the mold; casting the cement slurry in the core mold to obtain a cement sample; enabling the cement sample to be in a sealed to wait for solidification; when the cement sample is in a semi-solidified state and has plasticity, taking the core mold down, and cutting the cement sample with a steel wire according to a fracture direction required by an experiment, such that desired fractures are formed in places that are cut by the steel wire; and (8) keeping a cement sample isolated from the outside world, and acquiring the large model fractured core whose original oil-water saturation is maintained, after the solidification of the cement sample is completed.

Beneficial Effects

Compared with the prior art, the present invention has the following beneficial effects:
(1) the present invention provides a method for establishing original saturation in a cement core;
(2) The present invention provides a method for establishing saturation and a mold in one step; and
(3) by adjusting a ratio of cement, quartz sand, water to oil, the present invention can control the porosity and permeability parameters and the oil saturation of the core, control the distribution of fractures while manufacturing the core, and simulate fractured carbonates or sandstone better.

DETAILED DESCRIPTION

Embodiment of the Invention

The present invention will be further described below according to an example.

Example 1

A direct method for manufacturing a large model fractured core and maintaining original oil-water saturation comprises the following steps:

(1) determining the size, volume $V_o$ porosity $\varphi$, permeability K, oil saturation $S_o$ and water saturation $S_w$ of a core to the manufactured as 30 cm×30 cm×30 cm, 27,000 cm$^3$, 15%, 0.18 mD, 12.7% and 87.3% respectively, thereby acquiring the oil volume $V_o$ and the water volume $V_w$ of the core as 514.35 cm$^3$ and 3535.65 cm$^3$ respectively;

(2) determining the oil-water viscosity ratio of the formation as 10, preparing simulated oil according to the oil-water viscosity ratio of the formation under experimental conditions, and determining the oil density $\rho_o$ as 0.863 g/cm$^3$ and the water density $\rho_w$ as 1 g/cm$^3$, thereby determining the mass $m_o$ of oil for manufacturing the core as $m_o=V_o \times \rho_o$, i.e., 443.88 g;

(3) under the circumstance of no consideration of oil saturation; acquiring, through experiments, a water-cement ratio m and a cement-quartz sand ratio n, which are 0.4 and 1:3 respectively, based on the porosity $\varphi$ and the permeability K; and thus acquiring the mass of the used water, cement and quartz sand, i.e. a, b and c which are 6615 g, 16537.5 g and 49612.5 g respectively, under the circumstance of no consideration of oil saturation, i.e., the water saturation is 100%;

(4) under the circumstance of no consideration of oil saturation, filling pores of the core with water, such that $V_o$ and $V_w$ are both filled with water, and the water consumption at this time is a; while establishing oil saturation, continuing to fill $V_w$ with water, and replacing fluid, i.e., water in $V_o$ with oil, wherein the water volume is reduced by $V_o$ compared to that of a case before the oil saturation is established, and the consumption of water for manufacturing the core should be reduced by $V_o \times \rho_w$, i.e., 514.35 g; and thus acquiring the mass $m_w$ of water for manufacturing the core as $m_w = a - V_o \times \rho_w$, i.e., 6100.65 g;

(5) mixing oil, water and an emulsifier evenly to prepare a oil-in-water emulsion, wherein the emulsifier is a mixture prepared from sorbitan monooleate (Span-80) and polyoxyethylene sorbitan monooleate (Tween-80) in a mass ratio of 1:10, and accounts for 0.2%, i.e., 13.09 g, of the mass sum of oil and water;

(6) adding cement and quartz sand into the emulsifier in the step (5) and stirring evenly to obtain cement slurry, wherein the cement is Portland cement, and the quartz sand has a particle size of 80 mesh;

(7) applying simulated oil to the inner surface of a core mold, such that a thin oil film is formed on the inner surface of the mold; casting the cement slurry in the core mold to obtain a cement sample; when the cement sample is in a semi-solidified state, taking the core mold down, and cutting the cement sample in the middle of the cement sample with a steel wire in a horizontal direction, wherein desired fractures are formed in places that are cut by the steel wire; and (8) keeping the cement sample isolated from the outside world, and waiting for the completion of the solidification of the cement sample.

The large model fractured core manufactured by using the present invention has certain porosity and permeability, and can maintain the original oil-water saturation, and simulate the actual fractured carbonate rock reservoir better.

What is claimed is:

1. A direct method for manufacturing a large model fractured core and maintaining an original oil-water saturation, comprising the following steps:
   (1) determining a volume V, a porosity $\varphi$, a permeability K, an oil saturation $S_o$ and a water saturation $S_w$ of a fractured core to be manufactured, and determining an oil volume $V_o$ of the fractured core as $V_o = V \times \varphi \times S_o$, and an water volume $V_w$ of the fractured core as $V_w = V \times \varphi \times S_w$;
   (2) preparing a simulated oil according to an oil-water viscosity ratio of a formation under experimental conditions, and determining an oil density as $\rho_o$ and a water density as $\rho_w$, determining an oil mass $m_o$ for manufacturing the fractured core as $m_o = V_o \times \rho_o$;
   (3) under a circumstance of no consideration of the oil saturation; acquiring, through experiments, a water-cement ratio m and a cement-quartz sand ratio n based on the porosity $\varphi$ and the permeability K; and thus acquiring masses of used water, cement and quartz sand are a, b and c respectively, the circumstance of no consideration of the oil saturation is that the water saturation is 100%;
   (4) while establishing the oil saturation, continuing to fill the $V_W$ with water, and replacing a fluid in $V_o$ with an oil, the fluid is water, wherein the water volume is reduced by $V_o$, and a consumption of water for manufacturing the fractured core is reduced by $V_o \times \rho_w$; and thus acquiring a mass $m_w$ of water for manufacturing the fractured core as $m_w = a - V_o \times \rho_w$;
   (5) mixing the oil, water and an emulsifier evenly to prepare an oil-in-water emulsion, wherein the emulsifier accounts for 0.16% to 0.21% of a mass sum of the oil and the water;
   (6) adding the cement and the quartz sand into the emulsifier in the step (5) to form a mixed material and stirring the mixed material evenly to obtain a cement slurry;

(7) applying the simulated oil to an inner surface of a core mold to form a thin oil film on the inner surface of the core mold; casting the cement slurry in the core mold to obtain a cement sample; enabling the cement sample to be in a sealed state to wait for a solidification; when the cement sample is in a semi-solidified state, taking the core mold down, and cutting the cement sample with a steel wire according to a fracture direction required by experiments, desired fractures are formed in places that are cut by the steel wire; and (8) keeping the cement sample isolated from outside world, and acquiring the large model fractured core, the original oil-water saturation is maintained after the solidification of the cement sample is completed.

2. The direct method for manufacturing the large model fractured core and maintaining the original oil-water saturation according to claim 1, wherein in the step (3), the water-cement ratio is a mass ratio of the water to the cement, the water-cement ratio is ranging from 0.3 to 0.5; and the cement-quartz sand ratio is a mass ratio of the cement to the quartz sand, the cement-quartz sand ratio is ranging from 1:1 to 1:3.

3. The direct method for manufacturing the large model fractured core and maintaining the original oil-water saturation according to claim 1, wherein the emulsifier in the step (5) is a mixture prepared from a sorbitan monooleate and a polyoxyethylene sorbitan monooleate according to a mass ratio of 1:10.

4. The direct method for manufacturing the large model fractured core and maintaining the original oil-water saturation according to claim 1, wherein, in the step (6), the cement is Portland cement, and the quartz sand has a particle size of 80-120 mesh.

* * * * *